(12) United States Patent
Kim et al.

(10) Patent No.: US 10,168,266 B2
(45) Date of Patent: Jan. 1, 2019

(54) PORTABLE VISCOMETER AND METHOD OF MANUFACTURING CAPILLARY TUBE FOR MEASURING VISCOSITY

(71) Applicants: ELECTRONICS AND TELECOMMUNICATIONS RESEARCH INSTITUTE, Daejeon (KR); Korea Institute of Oriental Medicine, Daejeon (KR)

(72) Inventors: Wan Joong Kim, Daejeon (KR); Myeong Soo Lee, Daejeon (KR); Moon Youn Jung, Daejeon (KR); Dae-Sik Lee, Daejeon (KR); Ju Ah Lee, Daejeon (KR); Ho Young Lee, Daejeon (KR)

(73) Assignees: ELECTRONICS AND TELECOMMUNICATIONS RESEARCH INSTITUTE, Daejeon (KR); KOREA INSTITUTE OF ORIENTAL MEDICINE, Daejeon (KR)

( * ) Notice: Subject to any disclaimer, the term of this patent is extended or adjusted under 35 U.S.C. 154(b) by 270 days.

(21) Appl. No.: 15/013,926

(22) Filed: Feb. 2, 2016

(65) Prior Publication Data
US 2016/0223448 A1    Aug. 4, 2016

(30) Foreign Application Priority Data
Feb. 3, 2015    (KR) .................. 10-2015-0016696

(51) Int. Cl.
*G01N 11/12*    (2006.01)
*G01N 11/04*    (2006.01)
*G01N 11/00*    (2006.01)

(52) U.S. Cl.
CPC ............. *G01N 11/04* (2013.01); *G01N 11/12* (2013.01); *G01N 2011/008* (2013.01); *G01N 2011/0086* (2013.01)

(58) Field of Classification Search
CPC ................................ G01N 11/04; G01N 11/12
See application file for complete search history.

(56) References Cited

U.S. PATENT DOCUMENTS 1,780,952 A * 11/1930 Symmes ................. G01N 11/12
                                                    324/71.1
1,793,807 A *  2/1931 Klinger .................. G01N 11/12
                                                    73/54.15
(Continued)

FOREIGN PATENT DOCUMENTS

CN         1815179 A  *  8/2006
KR  20-1987-0010798     7/1987
(Continued)

OTHER PUBLICATIONS

English Translation of CN 1815179 A, Aug. 2006.*

*Primary Examiner* — Peter Macchiarolo
*Assistant Examiner* — Alexander Mercado

(57) ABSTRACT

Present disclosure provides a portable viscometer including a body and a measuring unit disposed on one side of the body. The measuring unit includes a capillary tube detachably attached to the measuring unit, and a first sensor and a second sensor, the first and second sensors being disposed adjacent to the capillary tube and vertically spaced apart from each other, and the capillary tube includes a bead therein. The bead may be fixed on the inner surface of the capillary tube by a fixing compound which is soluble in a fluid to be measured.

13 Claims, 7 Drawing Sheets

(56) References Cited

U.S. PATENT DOCUMENTS

| | | | | |
|---|---|---|---|---|
| 1,997,960 A * | 4/1935 | Bell | G01N 11/12 | 73/54.15 |
| 2,034,658 A * | 3/1936 | Jones | G01N 11/12 | 368/1 |
| 2,154,376 A * | 4/1939 | Cline | G01N 11/12 | 200/52 R |
| 2,320,218 A * | 5/1943 | Buckley | G01N 11/12 | 73/54.15 |
| 2,320,219 A * | 5/1943 | Buckley | G01N 11/12 | 73/54.15 |
| 2,388,387 A * | 11/1945 | Cohen | G01N 11/12 | 324/179 |
| 2,431,378 A * | 11/1947 | Eitzen | G01N 11/12 | 73/54.15 |
| 2,434,349 A * | 1/1948 | Cohen | G01N 11/12 | 324/179 |
| 2,609,682 A * | 9/1952 | Eitzen | G01N 11/12 | 73/54.15 |
| 2,672,047 A * | 3/1954 | Spear | G01N 11/12 | 73/54.16 |
| 2,955,459 A * | 10/1960 | Otakar | G01N 11/12 | 137/92 |
| 3,026,716 A * | 3/1962 | Connally, Jr. | G01N 11/12 | 73/382 R |
| 3,375,705 A * | 4/1968 | Kim | G01N 11/12 | 324/179 |
| 3,411,343 A * | 11/1968 | Baird, Jr. | G01N 11/12 | 73/54.17 |
| 3,707,871 A * | 1/1973 | Emmet | G01N 11/12 | 264/262 |
| 3,772,910 A * | 11/1973 | McGinn | G01N 11/12 | 73/54.19 |
| 4,003,255 A * | 1/1977 | Spencer | G01F 1/20 | 137/486 |
| 4,466,275 A * | 8/1984 | Thone | G01N 11/12 | 73/54.16 |
| 4,517,830 A * | 5/1985 | Gunn | G01N 11/12 | 73/54.15 |
| 4,852,388 A * | 8/1989 | Park | G01N 9/34 | 73/32 R |
| 5,203,203 A * | 4/1993 | Bryan | G01N 11/12 | 73/54.19 |
| 5,327,778 A * | 7/1994 | Park | G01N 11/12 | 73/54.15 |
| 6,134,394 A * | 10/2000 | Tsukamoto | G01N 11/08 | 118/689 |
| 2009/0216465 A1 * | 8/2009 | Millet | B01L 3/0217 | 702/50 |
| 2010/0144020 A1 | 6/2010 | Kim et al. | | |
| 2012/0142017 A1 | 6/2012 | Park et al. | | |
| 2015/0323440 A1 * | 11/2015 | Okkels | G01N 11/08 | 73/861 |

FOREIGN PATENT DOCUMENTS

| | | |
|---|---|---|
| KR | 10-0849942 B1 | 8/2008 |
| KR | 10-2011-0039823 A | 4/2011 |
| KR | 10-1458320 B1 | 11/2014 |

* cited by examiner

FIG. 4
FIG. 5
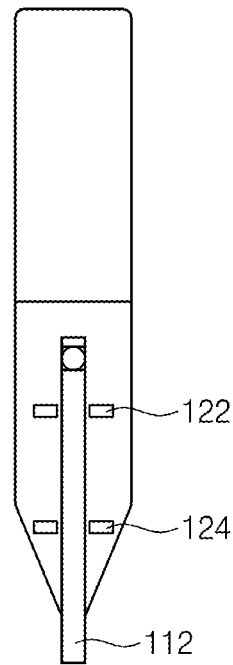
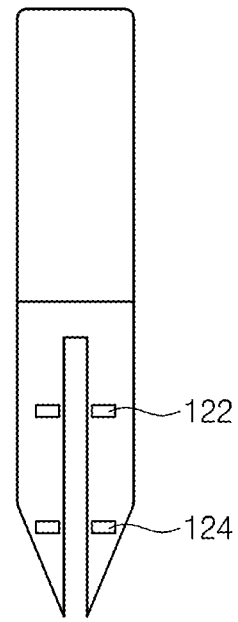
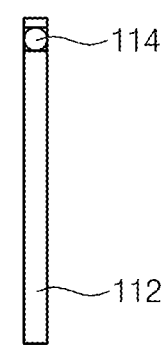

FIG. 8
FIG. 9
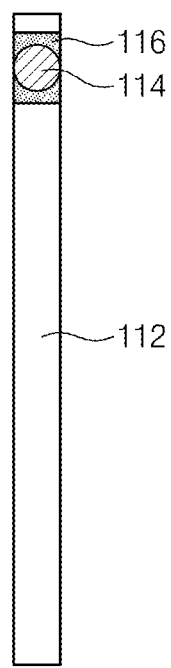
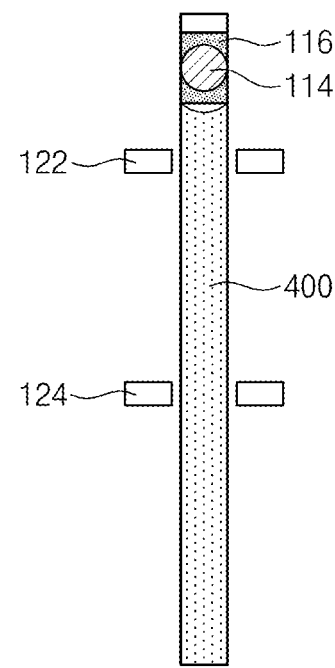

PORTABLE VISCOMETER AND METHOD OF MANUFACTURING CAPILLARY TUBE FOR MEASURING VISCOSITY

This U.S. non-provisional patent application claims priority under 35 U.S.C. § 119 of Korean Patent Application No. 10-2015-0016696, filed on Feb. 3, 2015, the entire contents of which are hereby incorporated by reference.

BACKGROUND

The present disclosure herein relates to a portable viscometer and a method of manufacturing a capillary tube for measuring viscosity.

Viscosity is a physical quantity that dominates fluidic properties of a fluid. The measurement of the viscosity is performed substantially in a liquid or a liquid substance containing a solid matter. The viscometer is widely used in foods, medicines, petroleum products, paints, inks, or various polymers.

The viscosity indicates the magnitude of difficulty in a fluid flow. When there are different velocities in the fluid flow, the velocities become equal to each other by collisions or interactions between molecules, which makes the energy to be lost. The process that involves such an energy loss is the viscosity. In the fluid flow in layers, a force between the layers and between the fluid and a wall adjacent thereto is referred to as a viscous force. A ratio of the viscous force to the velocity gradient in the fluid is defined as the viscosity.

The viscosity of blood, which may be changed according to constituents of blood, is an important factor in vascular diseases. Vascular diseases are increasing according to the changes of modern eating habits. Thus, interest in measurement of blood viscosity is increasing, and portable blood viscometers, which can be easily used by individuals, are attracting attention.

SUMMARY

The present disclosure provides a portable viscometer which has a portable simple structure and is capable of precisely measuring viscosity.

The present disclosure also provides a method of manufacturing a capillary tube used in the portable viscometer.

The purpose of the present invention is not limited to the aforementioned ones, and other purposes not mentioned above will be clearly understood by those skilled persons in the art from the following description.

An embodiment of the inventive concept provides a portable viscometer including a body and a measuring unit disposed on one side of the body. The measuring unit includes a capillary tube detachably attached to the measuring unit, and a first sensor and a second sensor which are disposed adjacent to the capillary tube. The capillary tube includes a bead therein.

In some embodiments, the capillary tube may have an inner diameter of 0.9 to 1.1 mm.

In some embodiments, the bead may have a diameter of 0.8 mm. The bead may be a spherical metal. The bead may be a magnetic material.

In some embodiments, the bead may be fixed on the inner surface of the capillary tube by a fixing compound. The fixing compound may be soluble in a fluid to be measured. The fixing compound may include at least one of bovine serum albumin, sodium hydroxide, sodium chloride, sodium citrate, sodium acetate, potassium phosphate, potassium nitrate, glucose, and lactose monohydrate.

In some embodiments, the first sensor and the second sensor each may be a photo interrupter or a magnetic sensor.

In some embodiments, the body may include a display or a controller.

In some embodiments, the portable viscometer may further include a cradle. The cradle may adjust an angle by which the viscometer is inclined from a vertical line normal to a horizontal plane.

An embodiment of the inventive concept provides a method of manufacturing a capillary tube for measuring viscosity, the method including injecting a fixing compound in a capillary tube, placing a bead in the fixing compound, and freeze-drying the capillary tube.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings:

FIGS. 4 and 5 are sectional views illustrating the portable viscometer according to an embodiment of the inventive concept;

FIGS. 6 to 8 are sectional views illustrating a method of manufacturing a viscosity measuring capillary tube according to an embodiment of the inventive concept; and FIGS. 9 to 11 are sectional views illustrating the operating principle of the portable viscometer according to an embodiment of the inventive concept.

DETAILED DESCRIPTION

Figure 1:
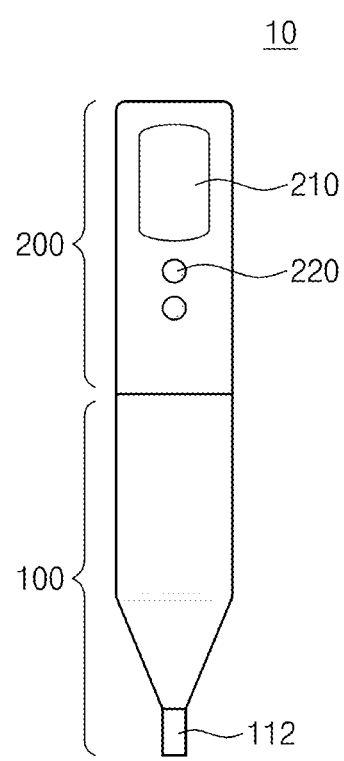
FIGS. 1 and 2 are schematic diagrams illustrating a portable viscometer according to an embodiment of the inventive concept.

In order to fully understand the constitution and effect of the present invention, preferred embodiments of the inventive concept will be described with reference to the accompanying drawings. However, the present invention is not limited to the embodiments disclosed below, but may be embodied in different forms and variously modified. Rather, these embodiments are provided so that this disclosure will be thorough and complete, and will fully convey the scope of the present invention to those skilled in the art. Those skilled in the art will understand that the inventive concept will be carried out in any suitable environment. Like reference numerals refer to like elements throughout the specification.

The terminology used herein is for the purpose of describing particular embodiments only and is not intended to be limiting of the invention. Terms in the singular form may include the plural forms unless otherwise stated. The terms "comprises" and/or "comprising", when used in this specification, specify the presence of stated features, steps, operations, and/or elements, but do not preclude the presence or addition of one or more other features, steps, operations, and/or elements.

In this specification, when a surface (or layer) is referred to as being on another surface (or layer) or substrate, it can be directly on the other surface (or layer) or substrate, or intervening layers may also be present.

Although terms such as first, second, and third are used to describe various regions, surfaces (or layers), and the like in various embodiments of this specification, these regions and surfaces should not be limited by these terms. These terms are only used to distinguish a predetermined region or surface (or layer) from another region or surface (or layer). An embodiment described and exemplified herein includes complementary embodiments thereof.

Additionally, the embodiments described herein will be explained with reference to sectional views and/or plan views as ideal exemplary views of the present invention. In the drawings, the dimensions of layers and regions are exaggerated for clarity of illustration. Thus, the exemplary views may have modified forms according to manufacturing techniques and/or allowable errors. Therefore, the embodiments of the present invention are not limited to the specific forms illustrated in the exemplary views, but may include other forms that may be created according to manufacturing processes. For example, an etched region illustrated as a rectangle may have rounded or curved features. Therefore, regions illustrated in the drawings have general properties, and the shapes thereof are intended to illustrate specific forms of element regions while not limiting the scope of the invention.

Unless otherwise defined, all terms (including technical and scientific terms) used herein have the same meanings as commonly understood by those skilled in the art.

Hereinafter, the present invention will be described in detail with reference to the accompanying drawings by way of explaining preferred embodiments of the inventive concept.

Figure 2:
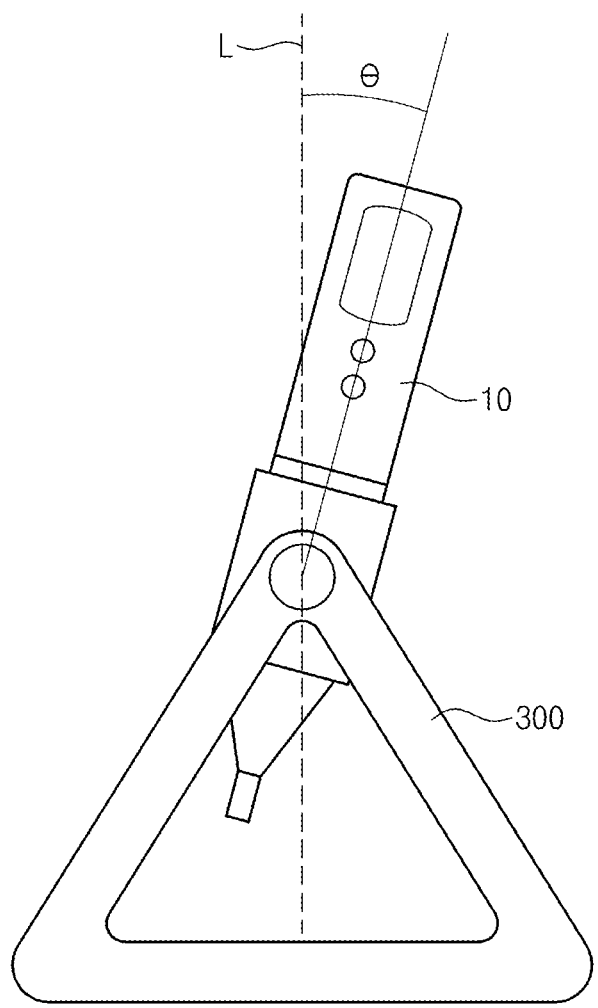
Figure 3:
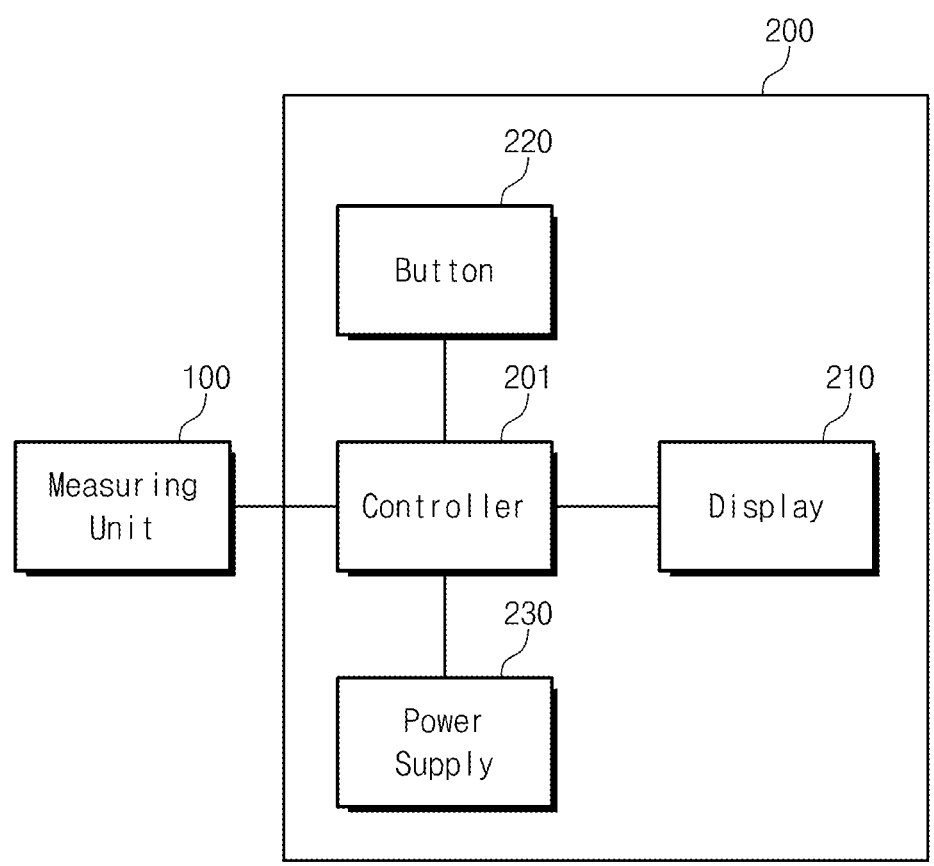
FIG. 3 is a conceptual view of the portable viscometer according to an embodiment of the inventive concept.

FIGS. 1 and 2 are schematic diagrams illustrating a portable viscometer 10 according to an embodiment of the inventive concept. FIG. 3 is a conceptual view of the portable viscometer 10 according to an embodiment of the inventive concept. FIGS. 4 and 5 are sectional views illustrating the portable viscometer 10 according to an embodiment of the inventive concept.

Referring to FIGS. 1 to 5, the portable viscometer 10 according to an embodiment of the inventive concept may include a measuring unit 100 and a body 200.

The measuring unit 100 may be provided on one side of the body 200. The measuring unit 100 may include a capillary tube 112, a first sensor 122, or a second sensor 124.

The capillary tube 112 may be provided in the measuring unit 100. The capillary tube 112 may be detachably attached to the measuring unit 100. The capillary tube 112 may have an inner diameter of 0.9 to 1.1 mm. The capillary tube 112 may have an outer diameter of 1.0 to 2.0 mm. The capillary tube 112 may be made of glass. The capillary tube 112 may include a bead 114 therein.

The bead 114 may be a spherical body. For example, the bead 114 may be a spherical metal. Alternatively, the bead 114 may be a spherical magnetic material. The bead 114 may have a diameter less than the inner diameter of the capillary tube 112. For example, the bead 114 may have a diameter of 0.8 mm. The bead 114 may be fixed in the capillary tube 112. For example, the bead 114 may be fixed in the capillary tube 112 using a fixing compound 116. The fixing compound 116 may be soluble in a fluid 400 to be measured. For example, when the fluid 400 to be measured is blood, the fixing compound 116 may include at least one of bovine serum albumin, sodium hydroxide, sodium chloride, sodium citrate, sodium acetate, potassium phosphate, potassium nitrate, glucose, or lactose monohydrate.

The first sensor 122 and the second sensor 124 may be disposed adjacent to the capillary tube 112. The first sensor 122 and the second sensor 124 may be spaced apart from each other. The first sensor 122 and the second sensor 124 may detect the bead 114 in the capillary tube 112. For example, the first sensor 122 and the second sensor 124 each may be a photo interrupter. That is, the first sensor 122 and the second sensor 124 each may have an optical transmitter and an optical receiver facing the optical transmitter. The bead 114 blocks light which is directed to the optical receiver from the optical transmitter, so that the movement of the bead 114 can be detected. When the bead 114 is a spherical magnetic material, the first sensor 122 and the second sensor 124 each may be a magnetic sensor. For example, the first sensor 122 and the second sensor 124 each may be a coil. That is, the movement of the bead 114 may be detected from a current change caused by the movement of the spherical magnetic material.

The body 200 may include a controller 201, a display 210, and buttons 220. The controller 201 may receive signals from the first sensor 122 and the second sensor 124 and may calculate the velocity of the bead 114. The controller 201 may calculate the viscosity of a fluid 400 to be measured, using the following equation.

$$v_{TS} = \frac{(\rho_p - \rho_f)g}{18\mu}d^2$$

where $v_{TS}$ is a final sedimentation velocity, $\rho_p$ is the density of a bead, $\rho_f$ is the density of a fluid, g is the gravitational acceleration, d is the diameter of the bead, $\mu$ is the viscosity of the fluid.

The display 210 may display the measured viscosity.

The portable viscometer 10 may further include a power supply 230.

A cradle 300 on which the portable viscometer 10 can be mounted may be provided. The portable viscometer 10 including the measuring unit 100 and the body 200 may be mounted on the cradle 300. The cradle 300 may adjust an angle ($\theta$) by which the viscometer is inclined from a vertical line L normal to a horizontal plane. For example, the portable viscometer 10 mounted on the cradle 300 may be adjusted in a range of 10 to 90°. The angle ($\theta$) of the portable viscometer 10 may be reflected in the viscosity calculation of the controller 201. The measurement may be performed with the angle ($\theta$) being adjusted according to a viscosity range of a fluid 400 to be measured. For example, when the fluid 400 to be measured is blood, the measurement may be performed with the portable viscometer 10 being rotated by an angle ($\theta$) of 20 to 30°.

Figure 6:
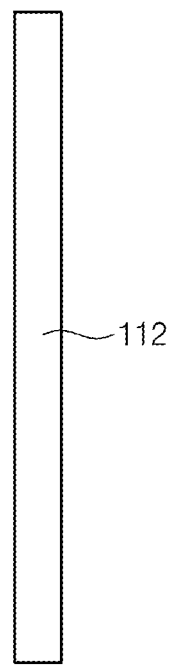
Figure 7:
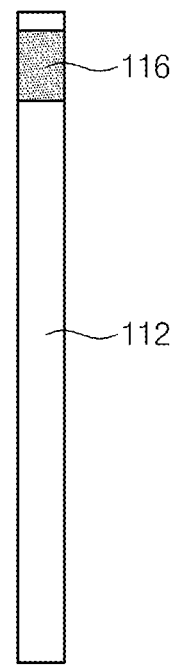

The capillary tube 112 of the portable viscometer according to an embodiment of the inventive concept may be manufactured according to the following procedure. FIGS. 6 to 8 are sectional views illustrating a method of manufacturing a viscosity measuring capillary tube according to an embodiment of the inventive concept.

Referring to FIG. 6, a capillary tube 112 is provided. The capillary tube 112 may have an inner diameter of 0.9 to 1.1 mm. The capillary tube 112 may have an outer diameter of 1.0 to 2.0 mm. The capillary tube 112 may be made of glass.

Referring to FIG. 7, a fixing compound 116 is injected to one side in the capillary tube 112. The fixing compound 116 may be well soluble in a fluid 400 to be measured. For example, when the fluid 400 to be measured is blood, the fixing compound 116 may include at least one of bovine serum albumin, sodium hydroxide, sodium chloride, sodium citrate, sodium acetate, potassium phosphate, potassium nitrate, glucose, or lactose monohydrate.

Referring to FIG. 8, the bead 114 is disposed in the fixing compound 116. The bead 114 may be a spherical body. For example, the bead 114 may be a spherical metal. Alternatively, the bead 114 may be a spherical magnetic material. The bead 114 may have a diameter less than the inner diameter of the capillary tube 112. For example, the bead 114 may have a diameter of 0.8 mm. The capillary tube 112 including the bead 114 and the fixing compound 116 may be freeze-dried. For example, when the fixing compound 116 is bovine serum albumin, the capillary tube 112 may be cooled for 1 hour at −40° C. For example, when the fixing compound 116 is bovine serum albumin, the capillary tube 112 may be dried for 3 hours at −40° C.

Figure 10:
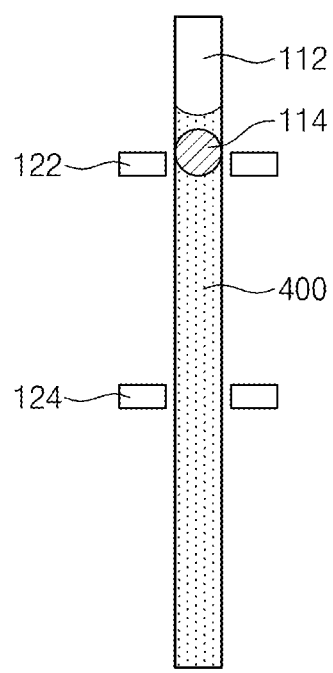
Figure 11:
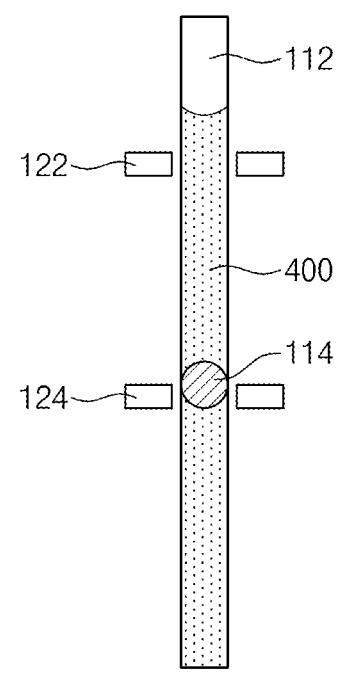

The operating principle of the portable viscometer 10 according to an embodiment of the inventive concept may be explained according to the following description. FIGS. 9 to 11 are sectional views illustrating the operating principle of the portable viscometer 10 according to an embodiment of the inventive concept.

Referring to FIG. 9, a fluid 400 to be measured is drawn from a direction opposite to the bead 114 in the capillary tube 112. For example, the fluid 400 to be measured may be drawn into the capillary tube 112 by the capillary phenomenon. The fluid 400 to be measured may contact the fixing compound 116 in the upper portion of the capillary tube 112.

Referring to FIGS. 10 and 11, the fixing compound 116 may be soluble in the fluid 400 to be measured. When the fixing compound 116 is dissolved, the bead 114 may fall free. The falling bead 114 may pass through a sensing range of the first sensor 122 and the second sensor 124. For example, when the first sensor 122 and the second sensor 124 each are a photo interrupter, time for the bead 114 to pass the distance between the first sensor 122 and the second sensor 124 is measured. That is, the bead 114 blocks light which is directed to the optical receiver from the optical transmitter in each of the first sensor 122 and the second sensor 124, so that the movement of the bead 114 may be detected. Thus, the sedimentation velocity of the bead 114 may be calculated. Alternatively, when the first sensor 122 and the second sensor 124 each are a magnetic sensor and the bead 114 is a magnetic material, the sedimentation velocity of the bead 114 may be calculated through an induced electromotive force generated by a magnetic field change according to the sedimentation of the bead 114. For example, the first sensor 122 and the second sensor 124 each may be a coil. That is, the movement of the bead 114 may be detected from a current change caused by the movement of the bead 114.

Using a replaceable capillary tube according to an embodiment of the present invention may allow structural simplification of a portable viscometer and contribute to simplicity of use in the portable viscometer. Furthermore, the portable viscometer can be used in various fluids, and thus ensure the versatility.

Although preferred embodiments of the present invention have been described with reference to the accompanying drawings, those skilled in the art will understand that the present invention can be implemented in other specific forms without changing the technical spirit or essential features thereof. Therefore, it should be understood that the above-described embodiments are exemplary and non-limiting in all aspects.

What is claimed is:

1. A portable viscometer comprising:
a body; and
a measuring unit disposed on one side of the body,
wherein the measuring unit comprises:
a detachable capillary tube; and
a first sensor and a second sensor which are disposed adjacent to the capillary tube including a bead therein,
wherein the bead is fixed on the inner surface of the capillary tube by a fixing compound.

2. The portable viscometer of claim 1, wherein the capillary tube has an inner diameter of 0.9 to 1.1 mm.

3. The portable viscometer of claim 1, wherein the bead has a diameter of 0.8 mm.

4. The portable viscometer of claim 1, wherein the bead is a spherical metal.

5. The portable viscometer of claim 4, wherein the bead is a magnetic material.

6. The portable viscometer of claim 1, wherein the fixing compound is soluble in a fluid to be measured.

7. The portable viscometer of claim 6, wherein the fixing compound includes at least one of bovine serum albumin, sodium hydroxide, sodium chloride, sodium citrate, sodium acetate, potassium phosphate, potassium nitrate, glucose, or lactose monohydrate.

8. The portable viscometer of claim 1, wherein the first sensor and the second sensor each include a photo interrupter or a magnetic sensor.

9. The portable viscometer of claim 1, wherein the body comprises a display and a controller.

10. The portable viscometer of claim 1, further comprising a cradle.

11. The portable viscometer of claim 10, wherein the cradle is capable of adjust an angle by which the viscometer is inclined from a vertical line normal to a horizontal plane.

12. A portable viscometer comprising:
a body;
a detachable capillary tube that includes a bead that is fixed to an inner surface of the capillary tube by a fixing compound; and
a first sensor and a second sensor which are disposed adjacent to the capillary tube.

13. The portable viscometer of claim 12, wherein the fixing compound is soluble in a fluid to be measured.

\* \* \* \* \*